United States Patent

Watson

(10) Patent No.: US 6,764,443 B1
(45) Date of Patent: Jul. 20, 2004

(54) LARYNGOSCOPE

(76) Inventor: Geoffrey Wilfred Watson, Thimble Hall, Whaddon Lane, Owslebury, Winchester SO21 1JJ (GB)

( * ) Notice: Subject to any disclaimer, the term of this patent is extended or adjusted under 35 U.S.C. 154(b) by 0 days.

(21) Appl. No.: 10/031,885

(22) PCT Filed: Jul. 27, 2000

(86) PCT No.: PCT/GB00/02845
§ 371 (c)(1),
(2), (4) Date: Feb. 12, 2002

(87) PCT Pub. No.: WO01/06913
PCT Pub. Date: Feb. 1, 2001

(30) Foreign Application Priority Data

Jul. 28, 1999 (GB) .............................................. 9917597

(51) Int. Cl.[7] .............................................. A61B 1/267
(52) U.S. Cl. ........................ 600/197; 600/196; 600/190
(58) Field of Search ................................. 600/120, 185, 600/188, 190, 191, 193, 196, 197, 199; 604/43

(56) References Cited

U.S. PATENT DOCUMENTS

| | | | |
|---|---|---|---|
| 3,771,514 A | | 11/1973 | Huffman et al. |
| 4,306,547 A | * | 12/1981 | Lowell ........................ 600/188 |
| 4,384,570 A | * | 5/1983 | Roberts ........................ 600/187 |
| 4,425,909 A | * | 1/1984 | Rieser ......................... 600/197 |
| 5,036,835 A | | 8/1991 | Filli |
| 5,178,132 A | * | 1/1993 | Mahefky ...................... 600/194 |
| 5,184,603 A | * | 2/1993 | Stone .......................... 600/193 |
| 5,529,570 A | * | 6/1996 | Storz .......................... 600/199 |
| 5,551,946 A | * | 9/1996 | Bullard ........................ 600/194 |
| 5,571,071 A | | 11/1996 | Shapiro |
| 5,772,581 A | * | 6/1998 | Gaines ........................ 600/190 |
| 5,893,830 A | | 4/1999 | Zeitels |
| 5,938,591 A | * | 8/1999 | Minson ........................ 600/191 |
| 6,102,851 A | * | 8/2000 | Mellin ......................... 600/199 |
| 6,174,281 B1 | * | 1/2001 | Abramowitz ............... 600/196 |
| 6,217,514 B1 | * | 4/2001 | Gruen et al. ................ 600/185 |
| 6,231,505 B1 | * | 5/2001 | Martin ........................ 600/194 |
| 6,354,993 B1 | * | 3/2002 | Kaplan et al. .............. 600/188 |

FOREIGN PATENT DOCUMENTS

GB        2 191 949 A        12/1987

* cited by examiner

Primary Examiner—John P. Leubecker
(74) Attorney, Agent, or Firm—Gifford, Krass, Groh, Sprinkle, Anderson & Citkowski (57) ABSTRACT

A laryngoscope comprises a blade having a surface (17) for engaging the tongue of a patient by means of an operating handle (13) manipulated by an operator in which the operating blade (13) lies out of the plane normal to the tongue-contacting surface (17) of the blade. The laryngoscope substantially avoids the likelihood of a load acting on the patient's upper teeth.

15 Claims, 5 Drawing Sheets i)

PRIOR ART ii)

PRIOR ART

LARYNGOSCOPE

FIELD OF INVENTION

The present invention is generally concerned with an improved laryngoscope for the visualisation of the larynx and the vocal cords. The improved laryngoscope of the present invention is particularly, although not exclusively, suitable for use by physicians, especially by anaesthetists in procedures requiring the tracheal intubation of patients. The improved laryngoscope of the present invention may also be used in veterinary practice.

BACKGROUND OF THE INVENTION

The tracheal intubation of patients generally requires the precise positioning of the head of a supine patient and use of a laryngoscope in the mouth to manipulate the pharyngeal structures and prevent the tongue and epiglottis from obscuring the laryngeal opening. A laryngoscope may carry a light bulb or fibre optic light system so as to illuminate the glottis and facilitate visualisation of the laryngeal opening for passage of an endotracheal tube through the larynx into the trachea.

One problem with the use of prior art laryngoscopes, whether it be just for visualisation, or for tracheal intubation, arises from the fact that there is an inherent tendency in use, often accentuated by inexperience, poor technique or tiredness, for the operator to position, or maintain the position of the blade by applying a levering action to the operating handle. This levering action uses the patient's upper teeth as a fulcrum around which the blade of the laryngoscope is turned. Unfortunately this can exert undue pressure and is the cause of dental injury often accompanying procedures involving laryngoscopy. The levering action is more likely where long procedures or other conditions complicate the use of the laryngoscope, for example, where the patient has atypical anatomy of the mouth or the patient's jaw experiences muscular spasm.

This tendency to lever a laryngoscopic blade is well known to those skilled in the art and the results of such incorrect use are found to be lessened by providing the laryngoscopic blade with a widened or resilient back so as to spread the load that may be acting on the teeth.

Although the use of different laryngoscope blade designs, for example the McCoy levering blade, may in fact reduce the possibility of incorrect usage none entirely removes the risk. Consequently there is still a need to provide an improved laryngoscope for preventing or reducing damage to a patient's teeth during laryngoscopy.

The present invention addresses the problem of incorrect use of a laryngoscope and potential damage to teeth during laryngoscopy by providing an improved laryngoscope which at least reduces the risk that levering forces will be applied by the operator in use.

SUMMARY OF THE INVENTION

The present invention therefore provides a laryngoscope comprising a blade having a surface for engaging the tongue of a patient by means of an operating handle manipulated by the operator in which the said operating handle lies out of the plane normal to the tongue-contacting surface of the said blade.

Preferably the angle that the longitudinal axis of the said operating handle makes to the plane normal to the tongue-contacting surface of the said blade is adjustable.

In a preferred embodiment of the invention the said angle is 90°, that is, the longitudinal axis of the said operating handle is perpendicular to the plane normal to the tongue-contacting surface of the said blade.

In another embodiment of the invention the said blade and the said operating handle may be integrally formed.

In yet another embodiment of the invention the distance between the root of the said blade and the connecting end of the said operating handle is adjustable.

In still another embodiment the angle that the longitudinal axis of the operating handle makes to the longitudinal axis of the root of the blade is adjustable.

BRIEF DESCRIPTION OF THE DRAWINGS

Various embodiments of the invention will now be described by way of non-limiting example, with reference to the following drawings, in which FIGS. 1 i) and ii) are respectively comparative views in use of a prior art laryngoscope and a laryngoscope of the present invention;

FIGS. 2 i) and ii) are perspective views of an embodiment in which the blade, handle and thumb contacting surface are integrally formed;

FIGS. 6 i) and ii) are perspective views of a further embodiment of the invention.

FIGS. 7 i), ii) and iii) are perspective views of a further, and presently preferred embodiment of the invention carrying optical fibre lighting means.

DETAILED DESCRIPTION OF THE INVENTION

The positioning of the blade of the present invention requires the same net upward and forward movement of the blade as when a conventional laryngoscope is used. However by virtue of the position of the handle relative to the blade this is achieved according to the present invention by applying a force to the operating handle which includes a linear component and a rotary component.

That is when used on a supine patient, with the operator standing at the patient's head, facing the feet, the use of the laryngoscope of the present invention involves a movement pushing away from the operator with a forward and twisting motion on the operating handle rather than a forward and lifting motion as in correct usage of conventional laryngoscopes.

This twisting motion is in fact in substantially the same rotational direction as the levering motion that would occur in incorrect use of conventional laryngoscopes. However, it will be understood that the laryngoscope of the present invention substantially avoids the likelihood of a load acting on the upper teeth. The development of a pivot position at the back of the blade and on the patient's upper teeth can only occur through a movement in a direction opposite to the applied forces on the laryngoscope in use—that is by the deliberate pulling back of the handle towards the operator. By contrast, in conventional laryngoscopes a levering action can develop through even a small movement of the hand or arm which is often imperceptible to the operator.

Thus the laryngoscope of the present invention requires a premeditated action on the part of the operator before a load can act on the upper teeth of the patient. That is, the development of a load acting on the patient's upper teeth cannot be the result of a mere accidental extension of the appropriate action as is often the case with other laryngoscopes.

One advantage of the laryngoscope of the present invention is that the extended arm and wrist of an operator follows a much more relaxed and natural position than when using conventional laryngoscopes. The tendency, therefore to rest the arm and wrist by exerting a force upon the patient's upper teeth is consequently much less pronounced and the risk of damage to the patient's teeth still further reduced. Should however the operator wish to rest his arm it will be found that with a laryngoscope of the present invention, a resting position cannot be found.

Another, particular, advantage of the present invention lies in the treatment of patients who are obese or have short necks or who are in late pregnancy or are trauma victims immobilised in a cervical collar where access to the oral cavity is impeded by the patient's chest. One prior art laryngoscope, comprising a so-called "polio blade" in which the angle between the tongue contacting surface of the blade and the operating handle is greater than 90° but in the same plane, increases the tendency for the operator to apply an incorrect levering action. By contrast, use of the laryngoscope of the present invention overcomes the problem of access without applying levering forces to the teeth.

To assist in the positioning of the blade, the laryngoscope of the present invention may be provided with a thumb-contacting surface upon which a force can be more easily transmitted to the handle or blade by the action of the operator's thumb in turning the wrist. The thumb-contacting surface may also act so as to maintain the position of the blade in use.

However the use, nature, size and position of the thumb-contacting surface will be determined by a number of considerations not essential to the practice of the invention.

The thumb-contacting surface may be integral to or otherwise provided on the proximal end of the blade. Alternatively the thumb-contacting surface may be integrally formed in both the blade and the handle.

Preferably, however, the thumb-contacting surface is integral to or otherwise provided on the operating handle of the laryngoscope. Still more preferably, the thumb-contacting surface is attached toward the connecting end of the operating handle.

The thumb-contacting surface may, for example, be provided by a cavity including a raised portion. Alternatively, however, the thumb-contacting contacting surface may be provided by an attached or integrally formed plate member.

When using a laryngoscope of the present invention an operator may be conventionally positioned in relation to a patient and for a laryngoscopic blade to be conventionally orientated in the patient's mouth. By virtue of the relationship of the tongue-contacting surface of the blade to the operating handle, it will appear to the operator that the handle projects to one side or other of the patient's mouth (see FIG. 1).

Embodiments of the present invention may be formed either as a generally left handed or a generally right handed laryngoscope. It should be appreciated, however, that since most operators will use the laryngoscope in their left hand, the present description and drawings generally refers to left handed laryngoscopes.

In other embodiments of the present invention the lateral distance between the root of the blade and the connecting end of the operating handle is adjustable. The effective length of the blade may thus be varied with or without a change of blades according to the needs of the patient. Alternatively the longitudinal distance between the root of the blade and the connecting end of the handle may be adjustable. Of course the lateral and longitudinal distance between the root of the blade and the connecting end of the handle may both be adjustable.

In yet another embodiment of the invention the angle between the longitudinal axis of the major portion of the blade and the longitudinal axis of the operating handle is adjustable. Such adjustments as are therefore possible may serve to further improve the comfort of both patient and operator.

Of course the lateral and/or longitudinal distance between the root of the blade and the connecting end of the operating handle may be adjustable together with the angle between the longitudinal axes of the main portion of the blade and of the handle.

The invention also provides for the use of any type of laryngoscopic blade known in the art including Macintosh and Miller type blades which may or may not be adapted for the purposes of the invention.

The laryngoscope of the present invention may also carry, or be adapted to provide, lighting means such as are known in the art for directing light at or toward the distal end of the blade—for example, arrangements providing fibre optic cables or lamps or lamps and light conducting blades.

Preferably the laryngoscope of the present invention further comprises a lighting arrangement in which the blade is made from a transparent, light conducting material. A suitable light conducting blade is described in British Patent GB 2 296 436.

The laryngoscope of the present invention may also be made wholly or in part of any material known in the art, including materials of resilient nature. They may also comprise a range of handle and/or blade sizes and be suitable for use with adults, children or neonates as well as being suitable for use in veterinary practice.

Figure 1:
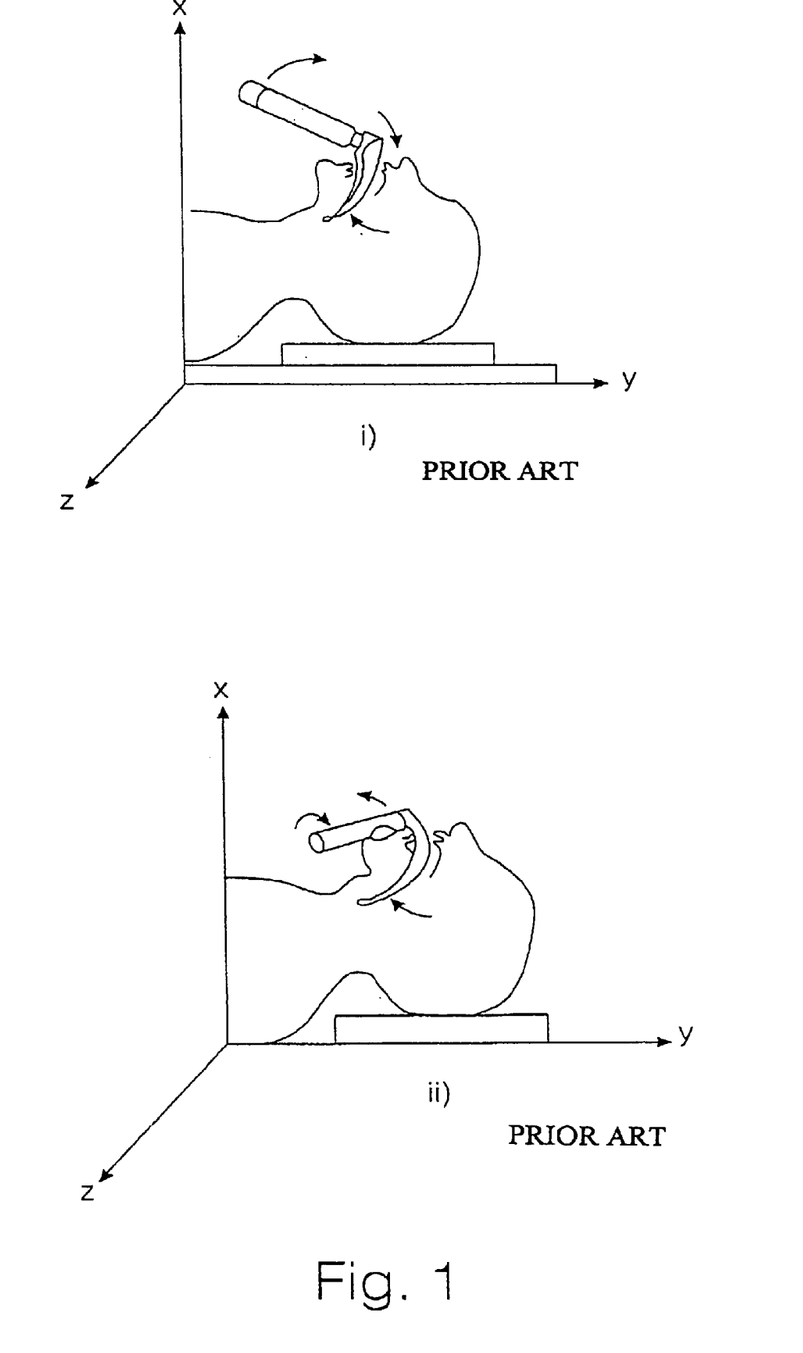

Referring now to the drawings, FIGS. 1 i) and ii) are generally intended to indicate the relationship between the operating handle of the present laryngoscope and the plane normal to the tongue-contacting surface of the blade. Noting then that the operator stands behind the head and facing the feet of the supine patient it is clear from FIG. 1 i) that the general length of the handle of a conventional laryngoscope is directed away from the operator towards the patient's feet. The handle is therefore in the plane xy, which is normal to the tongue-contacting surface of the blade (the arrows indicate the levering action of the blade in incorrect usage). In use the applied forces are directed towards the patient's teeth.

In the laryngoscope of the present invention, however, the handle lies in the plane xz and therefore out of the plane normal to the tongue-contacting surface of the blade (the arrows here show the direction of forces applied to the blade in use). In use the applied forces are directed away from the patient's teeth.

Figure 2:
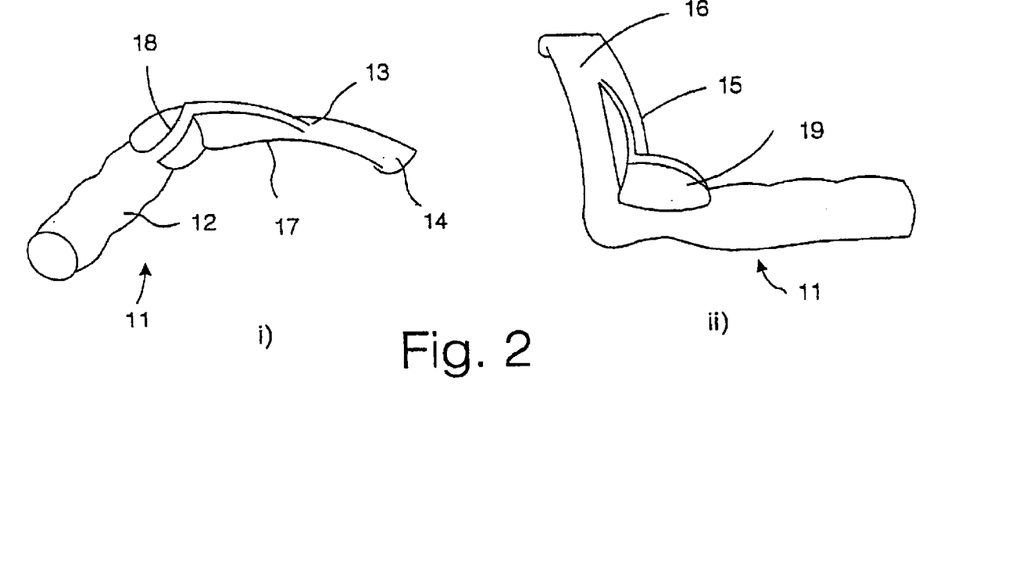

Referring now to FIGS. 2 i) and ii) the laryngoscope 11 shown comprises an operating handle 12 and laryngoscopic blade 13 integrally formed together. The blade is generally curved towards its distal end 14 and comprises an upright wall portion 15 and a flat portion 16 which together define a channel extending along the general length of the blade. The tongue-contacting surface of the blade, indicated by the number 17, lies on the opposite side of the surface of the blade containing this channel. The wall portion 15 is integral with a raised portion 18 of the handle and together they define a recess 19 in the surface of the handle and the blade. In use, the operator grips the handle so that the thumb is placed into the recess 19 and can exert a rotational force on the raised portion 18.

Figure 3:
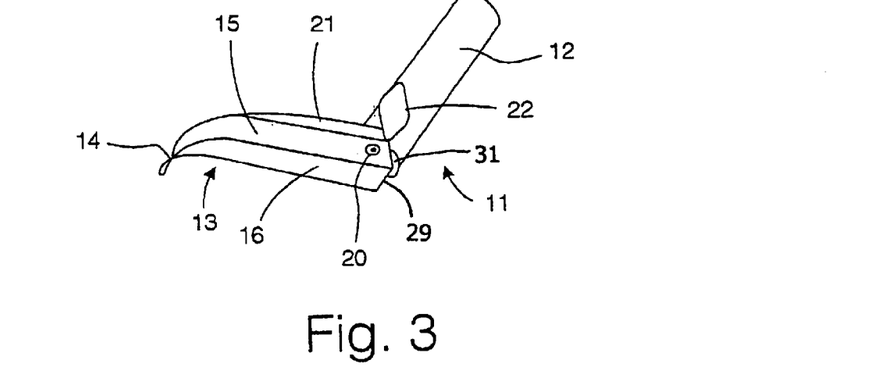
FIG. 3 is a perspective view of another embodiment.

Referring now to FIG. 3, the laryngoscope shown comprises a generally cylindrical handle 12 and a blade 13. The blade is similarly curved towards its distal end 14 and also comprises an upright wall portion 15 and a flat portion 16 which together define a channel extending along the general length of the blade. It will be noted that in this embodiment the upright wall portion 15 lies in the plane normal to the tongue-contacting surface of the blade. The blade is attached toward its proximal end to the flat top of the handle by screw thread engagement means 20. The blade, however, further comprises a flange portion 21 orthogonal to the upright wall portion 15 and tapering towards the distal end of the blade. Integrally formed at the proximal edge of the flange is a generally upright plate 22 one surface of which is a thumb-contacting surface for the operator.

Figure 4:
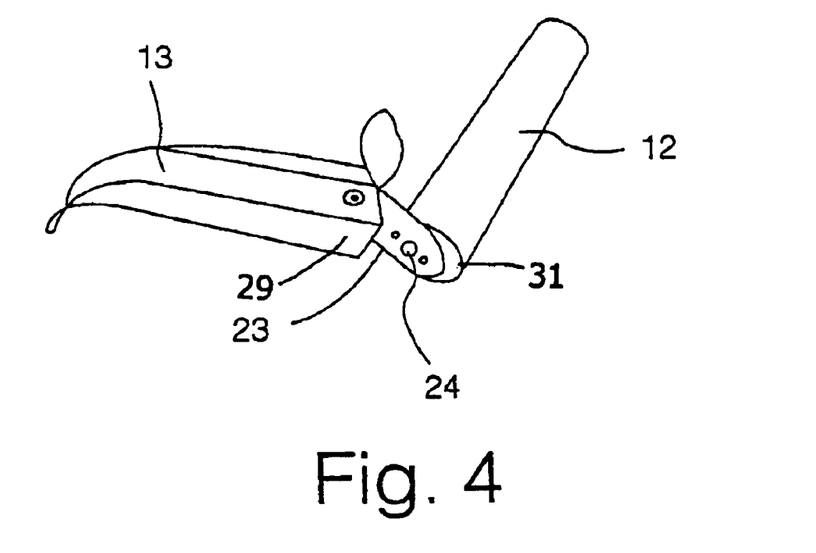
FIG. 4 is a perspective view of variant embodiment.

Referring now to FIG. 4, the blade of FIG. 3 and the flat part of the operating handle are attached, by screw thread engagement means, on opposite sides of an intervening linear bracket 23 comprising a plurality of apertures 24 along its length. The lateral distance between the root 29 of the blade and the connecting end 31 of the handle can thus be varied by moving the engagement means along the apertures. In addition the angle between the longitudinal axis of the major portion of the blade and the longitudinal axis of the handle may also be varied by rotating the bracket around its engagement means with one or other of the blade or the handle.

Figure 5:
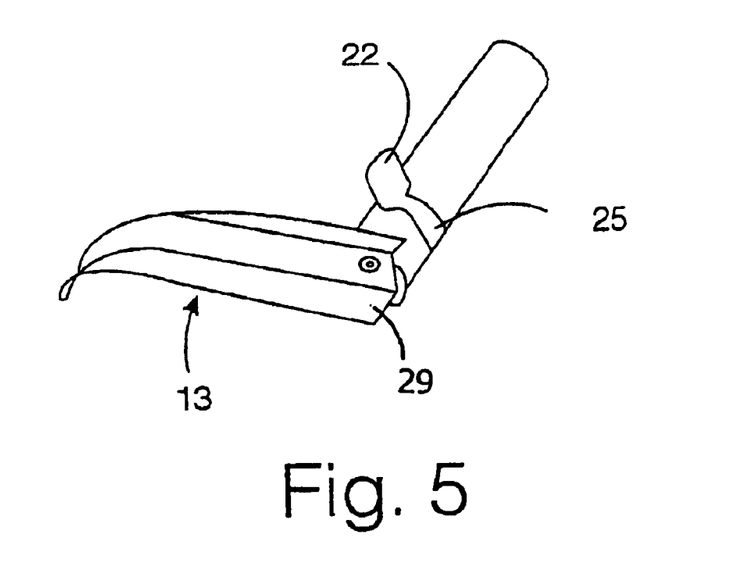
FIG. 5 is a perspective view of another embodiment of the invention.

Referring now to FIG. 5, there is shown a laryngoscope generally similar to that of FIG. 3 but having a blade 13 lacking a plate at the proximal edge of the flange portion. The plate 22 is, however, attached toward the proximal end of the operating handle, that is towards the blade, by attachment means 25.

Figure 6:
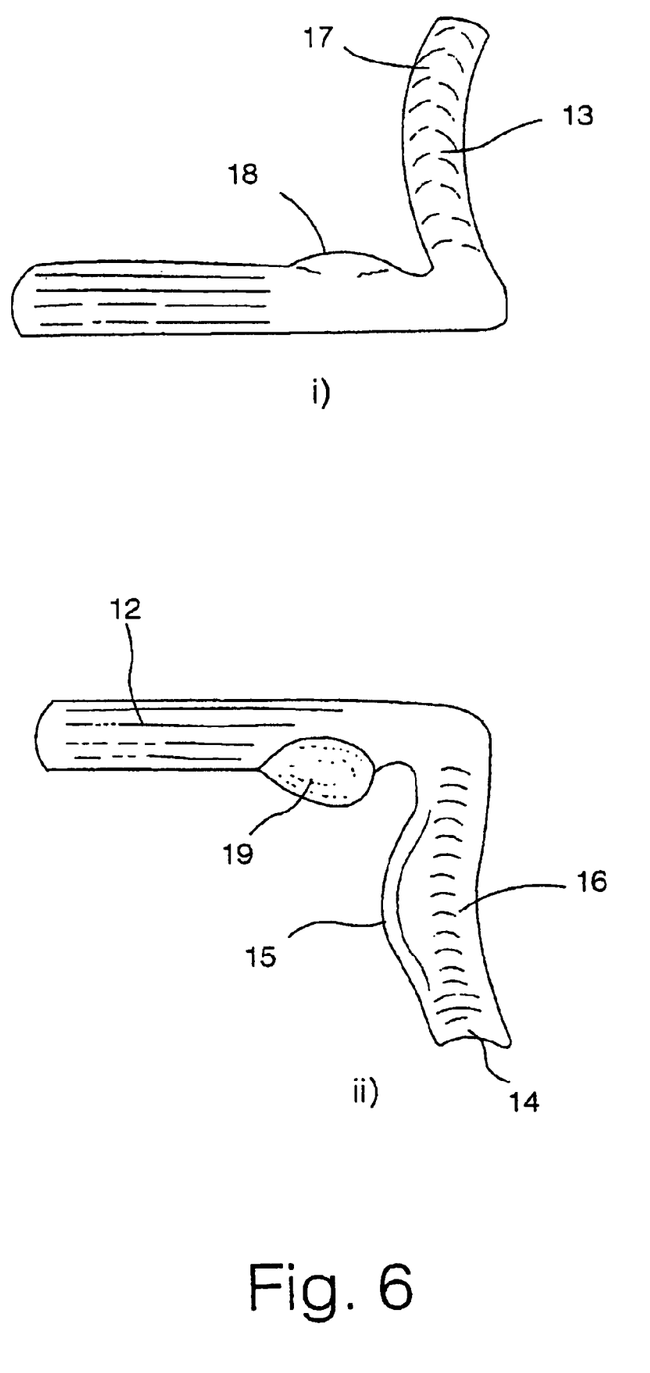

Referring now to FIGS. 6 i) and ii), two views of one embodiment of the invention illustrate a laryngoscope similar to that of FIG. 2. The blade 13 and handle 12 are integrally formed with the blade generally curved toward its distal end 14 and comprising an upright wall portion 15 and a concave portion 16 which together define a channel extending along the general length of the blade. The tongue-contacting surface 17 of the blade lies on the opposite surface to that of the channel. A raised portion 18 and recess 19, formed in and toward the proximal end of the handle, together define a thumb-contacting surface.

Figure 7:
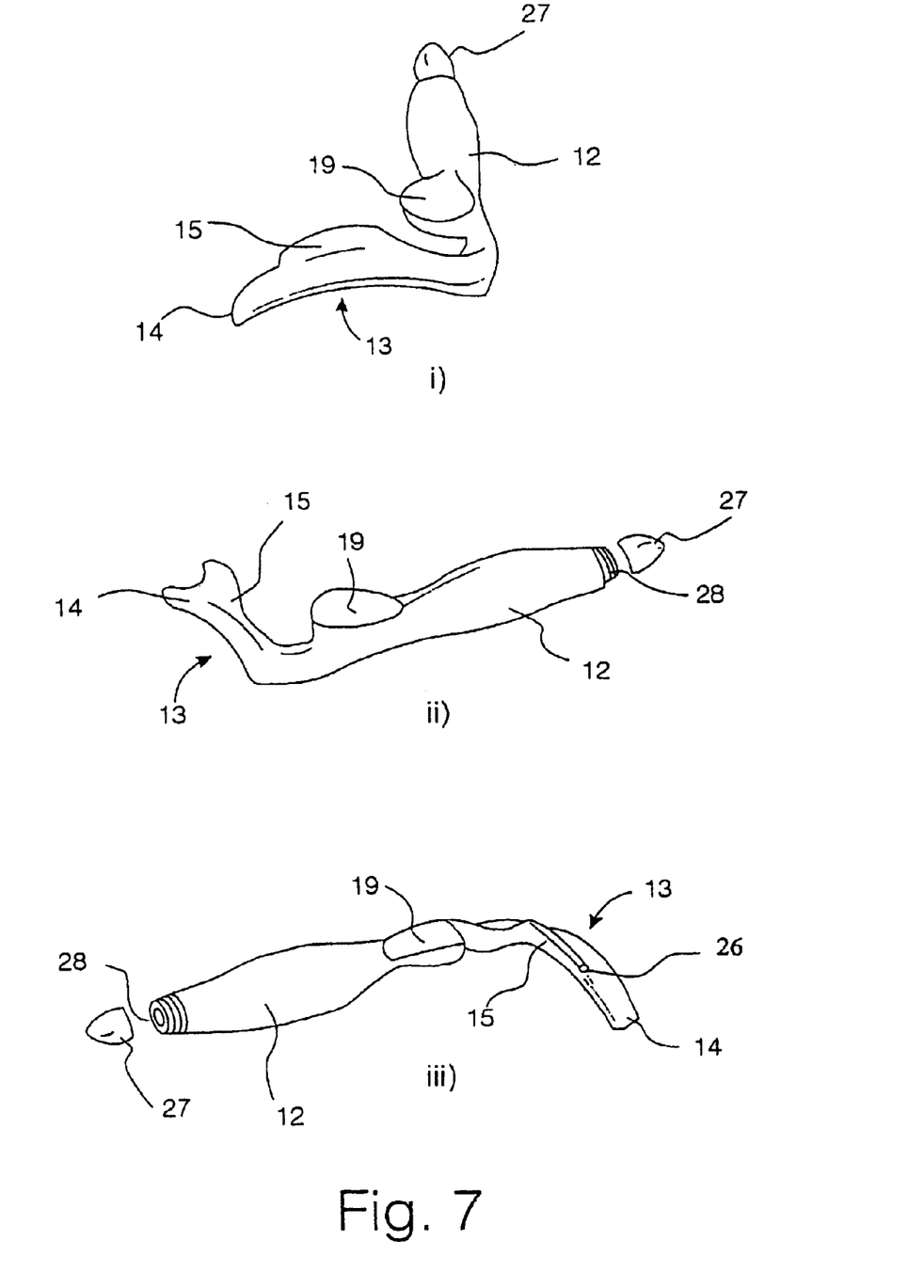

Referring now to FIGS. 7 i), ii) and iii), three views of the presently preferred embodiment illustrate a laryngoscope similar to that of FIG. 6. The handle 12 comprises a hollow section in communication with a channel extending through the upright wall portion 15 of the blade 13 and terminating at an aperture 26. Aperture 26 receives the end of an optical fibre extending along the channel to a battery powered light emitting electrical device arrangedin the hollow section of the handle 12. Handle 12 comprises an endcap 27, realisably connectable to the main body of the handle by a screw thread 28, allowing introduction of the battery and light emitting device. The main body is advantageously contoured so as to facilitate this arrangement and provide a comfortable fit to the operator's hand.

What is claimed is:

1. A laryngoscope comprising a blade having a surface for engaging the tongue of a patient by means of an operating handle manipulated by the operator, in which the said handle is fixed with respect to the blade and lies out of the plane normal to the tongue-contacting surface of the said blade so that laryngoscopy of a patient by manipulation of the handle involves at least a twisting motion by the operator about the longitudinal axis of the handle with the handle being held with the operator's thumb positioned at or near a root of the blade.

2. A laryngoscope as claimed in claim 1 wherein the said thumb-engaging part is offset with respect to the said longitudinal axis such that the thumb engaging part acts as a fulcrum when pressure is applied by the operator's thumb during the said twisting motion.

3. A laryngoscope as claimed in claim 1, wherein the said thumb-engaging part is provided on or integrally formed with the said operating handle.

4. A laryngoscope as claimed in claim 1, wherein the said thumb-engaging part is provided on or integrally formed with the said blade.

5. A laryngoscope as claimed in claim 1, in which the angle that the longitudinal axis of the said operating handle makes to the said plane is 90°.

6. A laryngoscope as claimed in claim 1 wherein the said blade is integrally formed with the said handle.

7. A laryngoscope as claimed in claim 1, wherein the distance between the root of the said blade and a connecting end of the said operating handle is adjustable.

8. A laryngoscope as claimed in claim 7, further comprising a link member linking the said root of the said blade and the said connecting end of the operating handle.

9. A laryngoscope as claimed in claim 1, further comprising lighting means for directing light at or toward the distal end of the blade.

10. A laryngoscope as claimed in claim 9, wherein the blade is formed from a transparent, light conducting material.

11. A laryngoscope as claimed in claim 10, wherein the said lighting means includes an optical fibre for transmitting light from a source thereof to the distal end of the blade.

12. A laryngoscope comprising a blade having a surface for engaging the tongue of a patient by means of an operating handle manipulated by the operator, in which the said operating handle is fixed with respect to the blade and lies out of the plane normal to the tongue-contacting surface of the said blade so that laryngoscopy of a patient by manipulation of the handle involves at least a twisting motion by the operator about the longitudinal axis of the handle, the said longitudinal axis being substantially coincident with a root of the blade.

13. A laryngoscope comprising a blade having a surface for engaging the tongue of a patient by means of an operating handle manipulated by an operator, in which the said operating handle is fixed with respect to the blade and extends from a root of said blade in a direction substantially perpendicular to the plane normal to the tongue contacting surface of the said blade and further comprising a thumb-engaging part positioned at or near the root of the blade and extending outwardly from the handle or the root of the blade.

14. A laryngoscope comprising a blade having a surface for engaging the tongue of a patient by means of an operating handle manipulated by the operator, in which said operating handle is fixed with respect to the blade and lies out of the plane normal to the tongue-contacting surface of the blade so that laryngoscopy of a patient by manipulation of the handle involves at least a twisting motion by the operator about the longitudinal axis of the handle with the handle being held with the operator's thumb positioned at or near a root of the blade and wherein the distance between the root of the blade and a connecting end of said operating handle is adjustable.

15. A laryngoscope comprising a blade having a surface for engaging the tongue of a patient by means of an operating handle manipulated by the operator, in which said operating handle is fixed with respect to the blade and lies out of the plane normal to the tongue-contacting surface of the blade so that laryngoscopy of a patient by manipulation of the handle involves at least a twisting motion by the operator about the longitudinal axis of the handle with the handle being held with the operator's thumb positioned at or near a root of the blade and wherein the distance between the root of the blade and a connecting end of said operating handle is adjustable; and a link member linking the root of the blade and the connecting end of the operating handle.

* * * * *

UNITED STATES PATENT AND TRADEMARK OFFICE
CERTIFICATE OF CORRECTION

PATENT NO. : 6,764,443 B1
DATED : July 20, 2004
INVENTOR(S) : Geoffrey Wilfred Watson It is certified that error appears in the above-identified patent and that said Letters Patent is hereby corrected as shown below:

Column 3,
Line 50, after "contacting" delete "contacting".

Column 6,
Line 8, after "blade" insert --, and further comprising a thumb-engaging part positioned at or near the root of the blade or the root of the blade. --

Signed and Sealed this

Twenty-second Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,764,443 B1
DATED : July 20, 2004
INVENTOR(S) : Geoffrey Wilfred Watson It is certified that error appears in the above-identified patent and that said Letters Patent is hereby corrected as shown below:

<u>Column 6,</u>
Line 8, replace "and further comprising a thumb-engaging part positioned at or near the root of the blade or the root of the blade." with -- and further comprising a thumb-engaging part positioned at or near the root of the blade and extending outwardly from the handle or the root of the blade. --.

Signed and Sealed this

Seventeenth Day of January, 2006

JON W. DUDAS
*Director of the United States Patent and Trademark Office*